United States Patent [19]

Hussain et al.

[11] Patent Number: 5,424,402
[45] Date of Patent: Jun. 13, 1995

[54] NON-DESTRUCTIVE METHOD FOR RADIOLABELLING BIOMOLECULES BY HALOGENATION

[75] Inventors: Anwar A. Hussain; Lewis W. Dittert, both of Lexington, Ky.

[73] Assignee: Board of Trustees of The University of Kentucky, Lexington, Ky.

[21] Appl. No.: 136,849

[22] Filed: Oct. 18, 1993

[51] Int. Cl.[6] ............... C07K 3/00; A61K 49/02
[52] U.S. Cl. ............... 424/1.53; 424/1.65; 424/1.89; 530/405; 530/409; 530/391.3; 436/542; 436/545
[58] Field of Search ............... 530/409, 405, 391.3; 424/1.65, 1.53, 1.89; 436/542, 545, 804, 808; 514/2

[56] References Cited

U.S. PATENT DOCUMENTS

| | | | |
|---|---|---|---|
| 3,867,518 | 2/1975 | Coffey et al. | 424/1.1 |
| 4,120,867 | 10/1978 | Akerkar et al. | 260/326.4 |
| 4,196,185 | 4/1980 | Focella et al. | 424/1.1 |
| 4,202,874 | 5/1980 | Akerkar et al. | 424/1.1 |
| 4,436,718 | 3/1984 | Smith | 424/1.1 |
| 4,450,149 | 5/1984 | Kabalka | 424/1.1 |
| 4,528,134 | 7/1985 | Stentz et al. | 260/112.7 |
| 4,591,552 | 5/1986 | Neurath | 435/7 |
| 4,874,601 | 10/1989 | Flanagan | 424/1.1 |
| 4,966,999 | 10/1990 | Coughlin et al. | 564/150 |
| 4,994,258 | 2/1991 | Burns et al. | 424/1.1 |
| 5,084,266 | 1/1992 | McKenzie et al. | |
| 5,171,666 | 12/1992 | Gutowski et al. | 530/387.3 |

OTHER PUBLICATIONS

Greenwood & Hunter, Biochem J., vol. 89, pp. 114–123, 1963.
Hunter & Greenwood, Nature, vol. 194, pp. 495–496, 1962.
Markussen, J. et al. "The Application of HPLC to the Analysis of Radioiodinated Tracers of Glucagon and Insulin", *Insulin: Chem., Struct. Funct. Insulin Relat. Horm., Proc. Int., Insulin Symp.*, (1980) pp. 161–168.
Boothe, Thomas E. et al. "The Preparation of No-carrier Added 4-[hu 131I] iodoantipyrine using chloramine-T", *J. Labelled Compd. Radiopharm.*, vol. 23, (1986) pp. 479–485.
Dickinson, Kenneth E., et al. "Photoaffinity Cross-linking of a Radioiodinated Probe [125]I-A55453, into Alpha 1-Adrenergic Receptors", *Mol. Pharmacol.*, vol. 26, No. 2, (1984) pp. 187–195.
Youfeng, He, et al. "A Comparative Study of Radioiodination of Simple Aromatic Compounds via N-Halo-Succinimides and Chloramine-T in Trifluoroacetic Anhydride (TFAA)", *J. Labelled Compd. Radiopharm.*, vol. 19, (1982) pp. 807–819.
Nakamura, Masahiro, et al. "Preparation and Evaluation of Radio Labelled Recombinant Human Interleukin-2 by Improved Chloramine-T. Method", *Radioisotopes*, vol. 40, No. 3, (1991) pp. 112–117.

*Primary Examiner*—Michael G. Wityshyn
*Assistant Examiner*—C. Sayala
*Attorney, Agent, or Firm*—Lowe, Price, LeBlanc & Becker

[57] ABSTRACT

A kit and method of non-destructively radiolabelling a biomolecule substrate by halogenation, including the steps of: a) reacting a secondary amine with a chlorinating agent to produce an N-chloro secondary amine, (b) reacting the N-chloro secondary amine with a salt of a radiolabelled halogen to produce a radiolabelled halogenating agent, (c) reacting a solution of the biomolecule substrate with the radiolabelled halogenating agent, and (d) recovering a radiohalogenated biomolecule from the reaction of step (c). The kit and method allow for more complete iodination with a lessening of side reactions such as decomposition of the biomolecule substrate to be labelled.

22 Claims, 3 Drawing Sheets

NON-DESTRUCTIVE METHOD FOR RADIOLABELLING BIOMOLECULES BY HALOGENATION

TECHNICAL FIELD

The present invention relates to a non-destructive method for radiolabelling biomolecules by halogenation. The method for halogenating or iodinating chemically sensitive substrates of the invention employs a secondary amine to reduce the oxidation potential of chloramine-T (sodium-p-toluene sulfo-chloramine or CAT) or other chlorinating agent. The present invention has been found to produce more complete halogenation or iodination with less side reaction than the traditional methods in which CAT is bonded to polymer beads. The method may be commercialized in kit form.

BACKGROUND ART

Frequently, it is desirable to radiolabel bioactive molecules with radioactive iodine or other halogens such as bromine. Most commonly, radioactive iodine is supplied in the form of KI* (wherein * represents a radioisotope of the halogen of interest, e.g., $I^{125}$ or $I^{131}$), and the labeling procedure involves reaction of KI* with chloramine-T (CAT) to release $I_2^*$ followed by addition of the substrate which then takes up the $I_2^*$ to form a radioiodinated product.

A major drawback to this procedure occurs when the substrate (compound to be labeled) is sensitive to oxidation or chlorination. Poor yields of the desired radiohalogenated or radioiodinated product and possibly complete decomposition of the substrate may occur through oxidation or chlorination, if residual CAT is left in the solution when the substrate is added.

The IODOBEADS® system (Pearce Chemical Company) attempts to avoid the problem of substrate decomposition by bonding the CAT onto polymer beads. A KI* solution is added to the beads and shaken to release free I*$_2$. A solution of the substrate is then added and shaken until the brown color disappears, then the beads are immediately filtered off to remove any residual CAT. The radioiodinated product is separated from the solution by preparative HPLC.

This system is only partially successful because CAT is released from the beads very rapidly. With sensitive substrates, if the manipulations are not carried out very quickly, significant amounts of CAT will appear in the solution and decompose the substrate. In many cases, the yields are very poor even though the procedure is carried out as quickly as possible. Finally, preparation of the polymer beads is relatively expensive.

Methods are known for radioiodinating molecules using chloramine-T (sodium-p-toluenesulfochloramine).

U.S. Pat. No. 3,867,518 to Coffey et al. describes a radioimmunoassay for insulin and further describes a method for the preparation of radioiodinated insulin using chloramine-T (sodium-p-toluenesulfochloramine) and a phosphate buffer. Coffey et al. does not disclose or suggest the use of piperidine or N-chloro-piperidine in a method of radioiodination.

U.S. Pat. No. 4,196,185 to Focella discloses an immunoassay for phencyclidine. To prepare radioiodinated N-(4-hydroxy-2-phenelthyl)-4-[1-piperidinyl)cyclohexyl] benzene acid sulfate, the compound was placed in ethyl acetate and water was added to a vial containing $Na^{125}I$. To this mixture was added chloramine-T. Then sodium meta bisulfite was added to stop the reaction.

U.S. Pat. No. 4,436,718 to Smith discloses an iodinating reagent. This patent discloses that N-chloro-4-methylbenzenesulfonamide or chloramine-T has long been used as the oxidant to mediate iodination reactions. The disclosure states that the use of chloramine-T has its drawbacks. The oxidant of Smith comprises a water insoluble bead having covalently attached to its surface molecules a chloramine group, with a size and shape of the bead being compatible with easy physical separation of the oxidant from a solution of the biological specimen. In the invention of Smith, chlorosulfonic acid, aqueous ammonia, and sodium hypochlorite yield the most preferred N-chlorobenzene sulfonamide functionality on the beads.

U.S. Pat. No. 4,450,149 to Kabalka et al. discloses a radiohalogenation method. In the method of Kabalka, the general procedure for iodination involved adding methanol and organoborane. Iodine-mono-chloride is then added. Sodium thiosulfate is then added to the mixture and the layers are dried over magnesium sulfite. Benzoyl chloride was added to 4-penten-1-ol in pyridine and stirred overnight at room temperature. Sequentially, diluted HCl was added and the mixture was saturated with aqueous $Na_2CO_3$ and water.

U.S. Pat. No. 4,528,134 to Stentz et al. discloses a method of iodinating insulin using chloramine-T. U.S. Pat. No. 4,591,552 to Neurath discloses the detection of hepatitis B surface antigen with labelled synthetic peptide. This patent discloses that if a peptide contains tyrosine it can be labelled by contacting the peptide with sodium $I^{125}$ in a buffer and then oxidizing it in the presence of chloramine-T. Neurath discloses that the peptide can be labelled with or without a solid support such as polystyrene beads. U.S. Pat. No. 4,775,638 to Haisma discloses a single vial technique for radiolabelling protein. Haisma discloses use of coupling agents such as iodogen (1,3,4,6-tetrachloro-3,6-diphenylglycuril), chloramine-T, lactoperoxidase and iodine monochloride. Iodination is conducted on an ion exchange resin.

U.S. Pat. No. 4,874,601 to Flanagan discloses a radiolabelling kit. The radiolabelling kit of Flanagan includes oxidizing agents such the sodium salt of N-chloro-p-toluenesolufonamide or chloramine-T, iodogen, or iodobeads (chloramine-T bonded to polystyrene beads). Flanagan does not disclose or suggest the use of piperidine or N-chloro-piperidine in a method of radioiodination.

U.S. Pat. No. 4,966,999 to Coughlin et al. discloses radiohalogenated compounds for site specific labelling. The process of Coughlin et al. includes an oxidant such as chloramine-T, iodobeads or iodogen. Coughlin does not disclose or suggest the use of piperidine or N-chloro-piperidine in a method of radioiodination.

U.S. Pat. No. 4,994,258 to Burns et al. discloses novel radiolabelled antagonists for pancreatic imaging. The radiolabelling process takes place in a sodium hydroxide solution of $Na^{125}I$ in the presence of cupric sulfate and ammonium sulfate.

U.S. Pat. No. 5,084,266 to McKenzie et al. discloses a method for tumor imaging utilizing a labelled tumor specific antibody and a non-tumor reactive antibody. McKenzie et al. found that the chloramine-T method for radiolabelling resulted in a greater loss of immunoreactivity than either the iodobead or enzymobead method. The enzymobead method was the method of choice for labelling in the method of McKenzie et al.

U.S. Pat. No. 5,171,666 to Gutowski et al. discloses the labelling of immunoglobulins using chloramine-T.

The publication of Markussen, J. et al., *Insulin: Chem., Struc. Funct. Insulin Relat. Horm., Proc. Int., Insulin Symp.* (1980) pp. 161–168 is entitled "The Application of HPLC to the Analysis of Radioiodinated Tracers of Glucagon and Insulin". This publication discloses the use of chloramine T and lactoperoxidase in the radioiodination of glucagon.

The publication of Boothe, Thomas E. et al., *J. Labelled Compd. Radiopharm.*, Vol. 23, (1986) pp. 479–485, entitled "The Preparation of No-carrier Added 4-[$^{131}$I] iodoantipyrine using chloramine-T. The publication discloses the use of chloramine-T and iodogen to iodinate antipyrine for use as a tracer in studying cerebral blood flow.

Dickinson, Kenneth E., et al., *Mol. Pharmacol.*, Vol. 26, No. 2, (1984) pp. 187–195. "Photoaffinity Crosslinking of a Radioiodinated Probe $^{125}$I-A55453, into Alpha 1—Adrenergic Receptors" discloses the radioiodination of an alpha1-adrenergic receptor probe. The method of radioiodination includes the use of chloramine-T and Na$^{125}$I.

Youfeng, He, et al., *J. Labelled Compd. Radiopharm.*, Vol. 19, (1982) pp. 807–819, "A Comparative Study of Radioiodination of Simple Aromatic Compounds via N-Halo-Succinimides and Chloramine-T in Trifluoroacetic Anhydride (TFAA)". This paper reports the comparative results of radioiodination performed using N-chlorotetrafluorosuccinimide, N-chlorosuccinimide, N-bromosuccinimide, and chloramine-T (CAT) as oxidizing agents with TFAA as an aprotic solvent. The study concluded that CAT is a superior oxidizing agent for the iodination of simple benzenes which are water insoluble but which are soluble in TFAA.

Nakamura, Masahiro, et al., *Radioisoptopes*, Vol. 40, No. 3, (1991) pp. 112–117, "Preparation and Evaluation of Radio Labelled Recombinant Human Interleukin-2 by Improved Chloramine-T Method". This publication discloses the use of a very small quantity of chloramine T to activate iodine (21 fold excess to iodine in molar ratio). This method of iodonation is useful for iodination of unstable peptides and proteins.

Baindur, Nandkishore, et al., *J. Med. Chem.*, Vol. 31, No. 11, (1988) pp. 2069–2071, "Discloses a Photoaffinity Label for the D-1 Dopamine Receptor". Radioiodination methodology used by Baidur includes the use of a modified NaI-Chloramine-T procedure. None of the above patents or publications disclose or suggest the use of piperidine or N-chloro-piperidine in a method of radioiodination.

The method of radiohalogenation of the present invention overcomes the deficiencies of prior art methods and provides an inexpensive method for radiohalogenating biomolecules which is non-destructive to the biomolecule.

DISCLOSURE OF THE INVENTION

Figure 1:
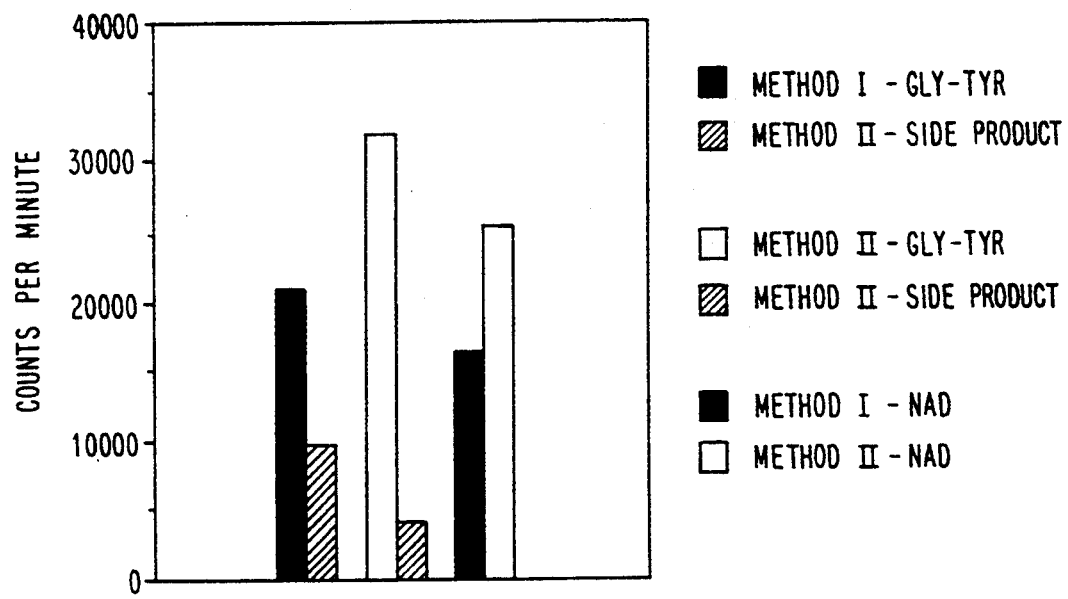
FIG. 1 shows a comparison of two methods of iodination of a Glysine-Tyrosine (Gly-Tyr) and an NAD analog using CAT—Example 1 and CAT+dimethylamine (DMA)—Example 2.

The present invention provides a method of nondestructively radiolabelling a biomolecule substrate by halogenation, comprising the steps of:

(a) reacting a secondary amine with a chlorinating agent to produce an N-chloro secondary amine, (b) reacting said N-chloro secondary amine with a salt of a radiolabelled halogen to produce a radiolabelled halogenating agent, (c) reacting a solution of said biomolecule substrate with said radiolabelled halogenating agent, and (d) recovering a radiohalogenated biomolecule from the reaction of step (c).

The invention also provides a method of producing a radiolabelled halogenating agent for non-destructively radiolabelling a substrate by halogenation, comprising the steps of:

(a) reacting a secondary amine with a chlorinating agent to produce an N-chloro secondary amine, and (b) reacting said N-chloro secondary amine with the salt of a radiolabelled halogen to produce a radiolabelled halogenating agent.

Additionally the invention provides a method of non-destructively radiolabelling a biomolecule substrate by radioiodination, comprising the steps of:

(a) mixing dry chloramine-T powder or chloramine-T bonded to polymer beads, with a solution of a secondary amine to reduce the oxidation potential of chloramine-T, to form a mixture, (b) shaking said mixture until all the chloramine-T powder has dissolved, (c) adding a solution of KI* or NaI* to said mixture, wherein I* represents a radioisotope of iodine, (d) shaking said mixture of step (c) for a time sufficient to release I$_2$* in solution, (e) adding a solution of said biomolecule substrate to said mixture, (f) shaking the resulting mixture of step (e) until the brown color disappears, and (g) recovering the radioiodinated biomolecule.

Advantageously, the invention provides a kit for non-destructively radiolabelling biomolecules by halogenation, comprising (a) a vial comprising a chlorinating agent, and (b) a vial comprising a solution of a secondary amine, (c) instructions for use.

The kit, preferably, further comprises a vial comprising a solution a salt of a radiolabelled halogen.

Also provided for is a method of non-destructively radiolabelling a biomolecule substrate by halogenation, comprising the steps of:

(a) mixing dry chloramine-T powder or chloramine-T bonded to polymer beads, with a solution of a secondary amine in molar excess over said chloramine-T powder or chloramine-T bonded to polymer beads, to form a mixture, (b) shaking said mixture until all the chloramine-T powder has dissolved, (c) adding a solution of KX* or NaX* to said mixture, wherein X* is a radioisotope of a halogen, (d) shaking said mixture of step (c) for a time sufficient to release X* in solution, (e) adding a solution of said biomolecule substrate to said mixture, (f) shaking the resulting mixture of step (e) until the color disappears, and (g) recovering the radiohalogenated biomolecule.

The radioactive iodide is preferably selected from $^{121}$I or $^{135}$I and radioactive bromide is preferably $^{77}$Br. It is preferred that the chloramine-T is in molar excess over KX* or NaX*, X* is a radioisotope of a halogen.

DESCRIPTION OF THE INVENTION

The invention provides a method of radiolabelling bioactive molecules with radioactive iodine or other radioactive halogens such as bromide. Radioactive iodide or bromide are preferred. Examples of radioactive iodide include $^{125}$I and $^{131}$I. An example of radioactive bromide is $^{77}$Br.

Bioactive molecule substrates which may be radiolabelled according to the method of the invention, include but are not limited to amino acids, peptides, proteins, drug molecules, antibodies, probes and diagnostic reagents.

The bioactive molecule substrates can be used in any process which requires a radiolabelled molecule. For example, such bioactive molecule substrates can be used in radioimmunoassays, enzyme-immunoassays, and for radiolabelling compounds to determine their location and/or distribution in animals, including humans.

Certain N-chloroamines have relatively low chlorine potentials, that is, they are relatively poor chlorinating and oxidizing agents. For example, N-chloro-piperidine (N-Cl-PIP) has a chlorine potential of 0.05, whereas CAT has a chlorine potential greater than 1. N-Cl-PIP is a much weaker oxidizing/chlorinating agent than CAT. N-Cl-PIP rapidly and quantitatively releases $I_2$ from $I^-$ in solution. This release is so facile that the active chlorine in N-Cl-PIP can be titrated iodometrically.

Thus, N-Cl-PIP could be used to release $I^*_2$ from $I^{*-}$ for radioiodination procedures. Unfortunately, N-Cl-PIP is not sufficiently stable either in aqueous solution or in its pure state to be packaged and sold commercially.

On the other hand, secondary amines, preferably dialkyl amines including but not limited to diisopropylamine, dibutylamine, dimethylamine, morpholine, methylethylamine, 2-(N)-methylamino heptane, N-isobutylamine, ethyl-n-butylamine, methyl-sec-butylamine, and piperidine (PIP), react rapidly and quantitatively with CAT to form N-chloro-secondary amines in solution. Any secondary amine may be used to practice the invention, and thus the invention need not be limited to the use of dialkylamines. For example, piperidine (PIP) reacts rapidly and quantitatively with CAT to form N-Cl-PIP in solution, as follows:

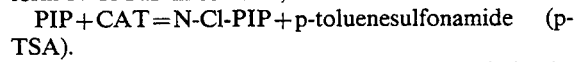

In a preferred embodiment, when the pH is in the range of 3 to 10, this reaction is complete in about 30 seconds or less. Since CAT is stable in the dry state, it can be used to produce N-Cl-PIP in situ immediately prior to use in the radiolabelling method of the invention.

Thus, present invention provides a method of nondestructively radiolabelling a biomolecule substrate by halogenation, comprising the steps of:

(a) reacting a secondary amine with a chlorinating agent to produce an N-chloro secondary amine, (b) reacting said N-chloro secondary amine with a salt of a radiolabelled halogen to produce a radiolabelled halogenating agent, (c) reacting a solution of said biomolecule substrate with said radiolabelled halogenating agent, and (d) recovering a radiohalogenated biomolecule from the reaction of step (c).

The radio-halogenated biomolecule may preferably be recovered by preparative high pressure liquid chromatography. The secondary amine may be selected from dialkylamines, selected from dimethyl amine, diethylamine, diisopropylamine, dibutylamine morpholine and piperidine (PIP).

A cation of the salt of the radiolabelled halogen may be selected from the group consisting of sodium, potassium, lithium, rubidium, cesium, magnesium, calcium and ammonium.

The chlorinating agent may be selected from chloramine-T, chloramine-T bonded to polymer beads, halazone, N-chlorosuccinimide, tetrachloroglycoluril, sodium hypochlorite, hypochlorus acid and elemental chlorine.

The bioactive molecule substrate may include amino acids, peptides, proteins, drug molecules, drug metabolites, antibodies, probes and diagnostic reagents.

The present invention provides a method for non-destructively radiolabelling a biomolecule substrate by halogenation, including steps of: (a) mixing dry chloramine-T powder or chloramine-T bonded to polymer beads, with a solution of a secondary amine in molar excess over chloramine-T powder, to form a mixture, (b) shaking the mixture until all the chloramine-T powder has dissolved, (c) adding a solution of KX* or NaX* to the mixture, wherein X* is a radioisotope of a halogen, (d) shaking the mixture of step (c) for a time sufficient to release X* in solution which preferably is about 30 seconds, (e) adding a solution of the biomolecule substrate to said mixture, (f) shaking the resulting mixture of step (e) until the color disappears, and (g) recovering the radiohalogenated biomolecule.

In an alternative embodiment, the invention provides a method for non-destructively radiolabelling a biomolecule substrate by radioiodination, comprising the steps of:

(a) mixing dry chloramine-T powder or chloramine-T bonded to polymer beads, with a solution of a secondary amine to reduce the oxidation potential of chloramine-T, to form a mixture, (b) shaking the mixture until all the chloramine-T powder has dissolved, (c) adding a solution of KI* or NaI* to the mixture, (d) shaking the mixture of step (c) for a time sufficient to release I* in solution which preferably is about 30 seconds, (e) adding a solution of the biomolecule substrate to said mixture, (f) shaking the resulting mixture of step (e) until the brown color disappears, and (g) recovering the radioiodinated biomolecule.

Dry chloramine-T powder or chloramine-T bonded to polymer beads may be mixed with the secondary amine in step (a). It is also preferred that the secondary amine is piperidine (PIP) buffered at about pH 6.0 in molar excess over chloramine-T powder.

Advantageously, the invention provides a kit for non-destructively radiolabelling biomolecules by halogenation, comprising (a) a vial comprising a solution of KI* or NaI*, and (b) a vial comprising dry chloramine-T powder or chloramine-T bonded to polymer beads in molar excess over KI*, (c) a vial comprising a solution of a secondary amine in molar excess over chloramine-T powder, (d) instructions for use.

Thus, the present invention provides for a kit for radioiodination of biomolecules. The kit preferably consists of two vials. Vial 1 contains a chlorinating agent such as dry CAT powder or the CAT bonded to polymer beads, and Vial 2 contains a solution of a secondary amine which is preferably, PIP buffered at pH 6.0. To radioiodinate a substrate, Vial 2 is added to Vial 1 and shaken until all the CAT particles have dissolved. KI* is then added and the mixture shaken for about 30 seconds or a time sufficient to release $I_2^*$ in solution.

A solution of the substrate, is then added and the mixture shaken until the color, brown color in the case of iodine, disappears. The radioiodinated product may be recovered by preparative HPLC in the manner known in the art.

After mixing Vial 1 and Vial 2, it is preferred to ensure that all CAT particles are dissolved before the substrate is added.

The kit should contain a secondary amine, such as PIP, in molar excess over CAT to ensure complete decomposition of the CAT before the substrate is added. CAT should be present in molar excess over KI* to ensure complete conversion of $I^{*-}$ to $I^*_2$.

According to the method of the invention it would not be necessary to hurry any step of this procedure since $I^*_2$ is relatively stable in solution and any reaction between residual N-Cl-PIP (or other chlorinated secondary amine) and the radioiodinated product would occur very slowly, if at all.

In a preferred embodiment the KI* is included in Vial 2, however, it may also be added separately from a third vial by the researcher during the procedure.

Below is a flow chart depicting an example of the radiohalogenation method of the invention. Radioiodine is used as an example. The molar quantities indicated below are intended to show ratios and are included for illustration only.

| TYPICAL FLOW CHART FOR RADIOHALOGENATION METHOD | |
| --- | --- |
| 1. Vial 1 - CAT (dry powder 2 mmol) + Vial 2 - Aqueous solution buffered at pH 6.0 containing PIP 3 mmol. | |
| 2. Mix and shake until ALL CAT PARTICLES are dissolved. | |
| 3. Add - KI* | 1 mmol |
| Substrate | 2 mmol |
| 4. Mix and stand for about 30 seconds. | |
| VIAL CONTENTS | |
| Vial 1 - Aqueous solution containing | |
| P-TSA | 2 mmol |
| N—Cl—PIP | 1 mmol |
| I*-Substrate (labeled) | 1 mmol |
| Substrate (unlabeled) | 1 mmol |
| | Treat with Sodium Thiosulfate |
| 5. Preparative HPLC to recover labeled substrate | |
| 6. Results in I*-Substrate (labeled) 1 mmol. | |

Several iodination experiments were run with various modifications of both the new non-destructive method as compared to a method using CAT bonded to polymer beads. The dipeptide, glycine-tyrosine (Gly-Tyr), and a nicotinamide adenine dinucleotide (NAD) analog were chosen as model substrates. The results show that, under optimum conditions, the method of the present invention resulted in up to 4 times more iodine being taken up by the substrate compared with methods employing CAT bonded to polymer beads. In the case of Gly-Tyr, the new method produced significantly less side reaction product.

Details of the methods and the exact compositions of the solutions are given at the end of this section. The results are shown as bar charts of counts per minute scraped from the thin layer chromatography (TLC) plates used to separate the iodinated products from the other reaction products.

DETAILED DESCRIPTION OF THE DRAWINGS

FIG. 1 shows that when CAT was used alone as the oxidizing agent (Method I, corresponding to the procedure of Example 1), the degree of iodination of the two substrates was significantly less than when dimethylamine (DMA) was mixed with the CAT one minute before adding the substrate and iodide (Method II, Example II). FIG. 1 also shows that the amount of a side reaction product formed during the reaction with Gly-Tyr was significantly reduced in the presence of DMA.

Figure 2:
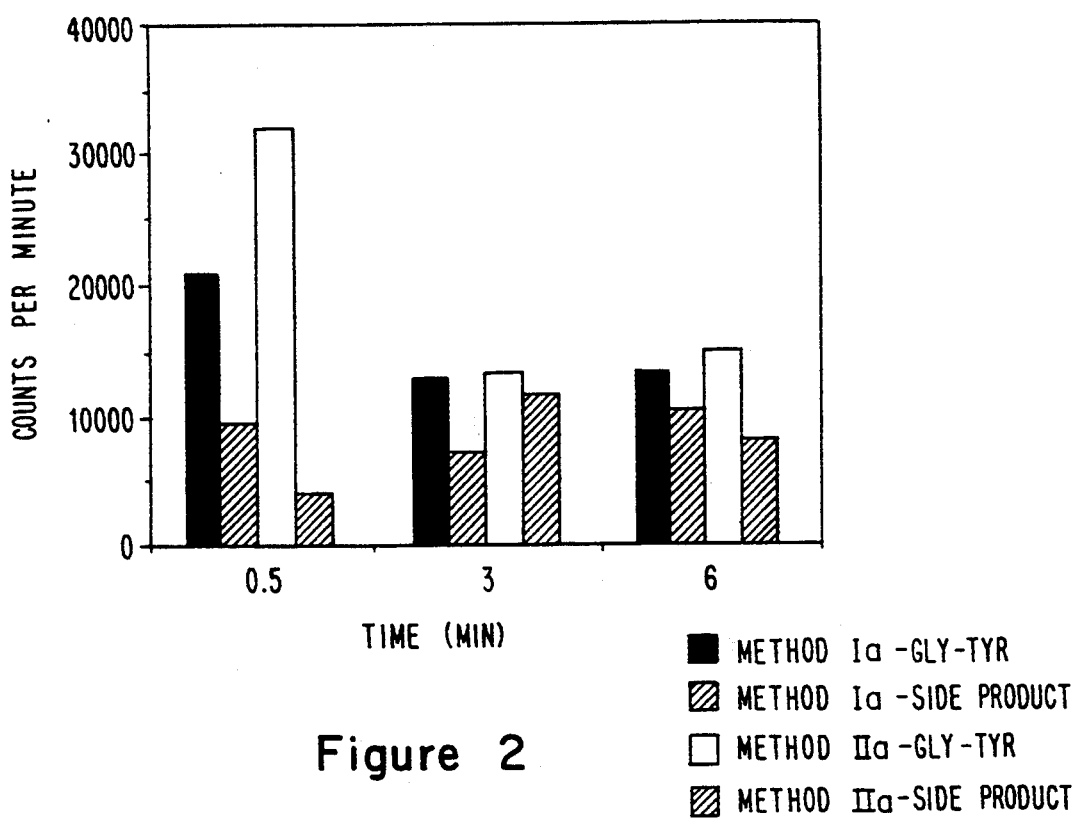
FIG. 2 shows the influence of incubation of the substrate-iodide-CAT (Example 1a) mixture or the substrate-iodide-CAT-DMA mixture (Example 2a) on the production of desired and side products for Gly-Try.

FIG. 2 shows that incubating either the substrate-iodide-CAT or the substrate-iodide-CAT-DMA system for longer than 30 seconds results in a lower yield of iodinated Gly-Tyr and a greater yield of side reaction product.

Figure 3:
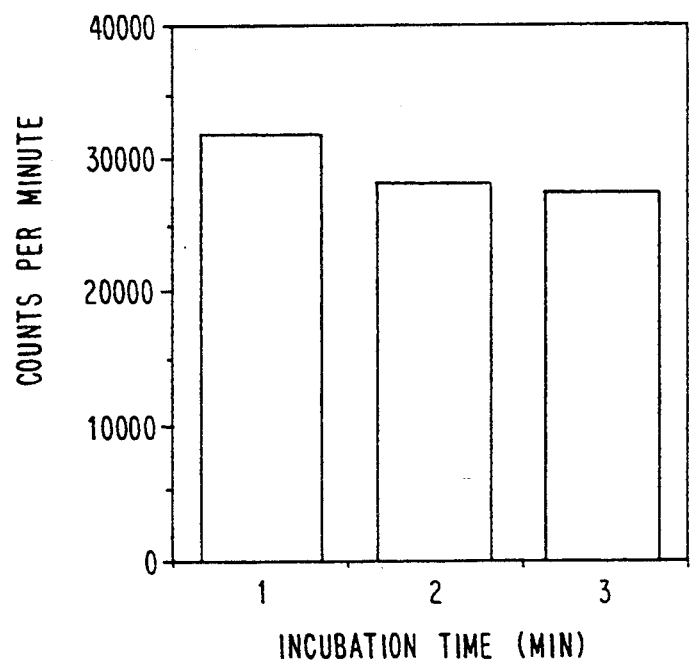
FIG. 3 shows the influence of time of preincubation of the CAT-DMA mixture before the introduction into the substrate iodine mixture on the production of the desired product for Gly-Tyr.

FIG. 3 shows that preincubation of the CAT-DMA mixture for 1, 2, or 3 minutes prior to adding the substrate and iodide has no effect on the degree of iodination of Gly-Tyr. These results suggest that CAT transfers all its chlorine to DMA in the first few seconds after the substances are mixed.

Figure 4:
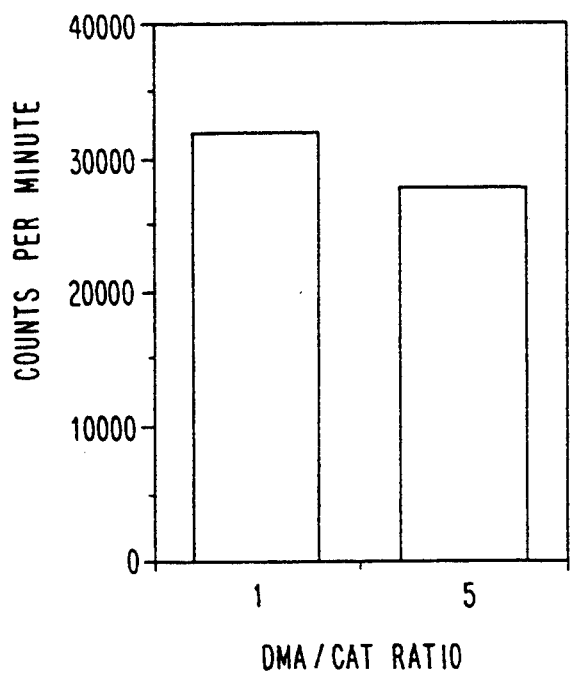
FIG. 4 shows the influence of the DMA/CAT ratio on the production of the desired product for Gly-Tyr.

FIG. 4 shows that increasing the ratio of DMA to CAT from 1 to 5 does not influence the degree of iodination of Gly-Tyr. This also suggests that DMA/CAT ratios greater than 1 may not be needed to protect substrates from decomposition.

Figure 5:
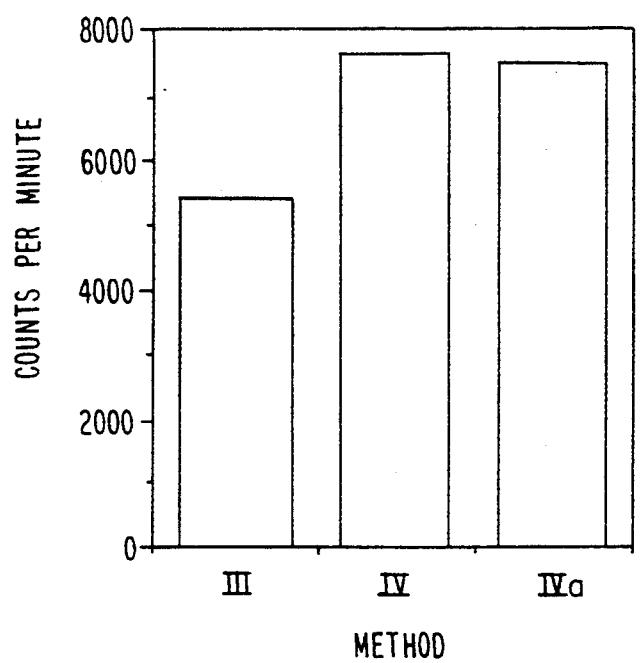
FIG. 5 shows the iodination of Gly-Tyr by three methods employing Iodobeads ®.

FIG. 5 shows the results of three methods employing Iodobeads® with Gly-Tyr. Method III, which employed Iodobeads® alone, gave significantly less iodinated product than Methods IV and IVa which employed Iodobeads®+DMA.

Figure 6:
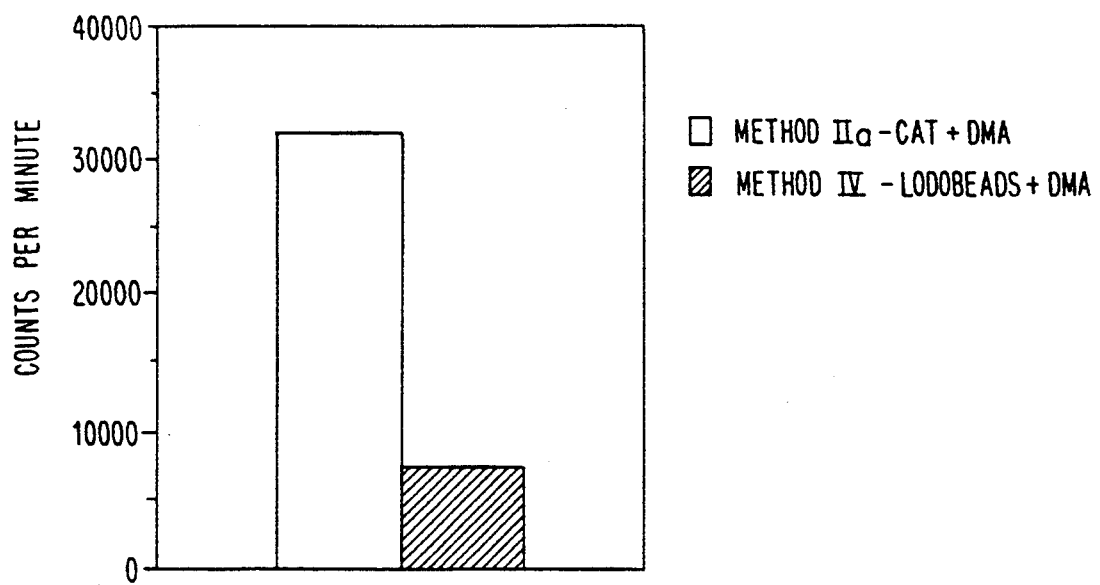
FIG. 6 shows a comparison of Example 2a (CAT+DMA solution) with Example 4 (Iodobeads ®+DMA) for iodination of Gly-Tyr.

FIG. 6 shows a comparison of Method IIa (CAT+DMA solution) with Method IV (Iodobeads®+DMA). The results show that Method IIa gives approximately four-fold greater iodination than that given by Method IV.

Note method numbers in the figures correspond to example numbers set forth below in the examples of the invention.

EXAMPLES

The examples set forth below correspond to the methods and their results indicated in the figures.

COMPARATIVE EXAMPLE I (CAT Solution Only)

5 μl of Substrate (Gly-Tyr) Solution OR
5 μl Substrate (NAD) Solution
+5 μl NaI Carrier Solution +5 μl NaI Labeled Solution
+10 μl CAT Solution
STIR 30 seconds
ADD 30 μl Sodium Thiosulfate Solution
REMOVE 30 μl aliquot
RUN thin layer chromatography (TLC)
For Glycine-Tyrosine: n-butanol:AcOH:H2O, 4:2:1
For NAD Analog: n-butanol:AcOH:H2O, 5:2:3
CUT BANDS from TLC
DISPERSE in 10 ml water
TRANSFER 2 μl of clear supernate to scintillation vials containing 10 ml Fischer Scintillation II liquid scintillation cocktail.
COUNT using a Packard Model 3375 Tri-Carb Liquid Scintillation Spectrometer.

INVENTION EXAMPLE II (CAT+DMA Solution) (Glycine-Tyrosine only)

Same procedures as Example I, except:
10 μl CAT Solution was mixed with 10 μl dimethylamine (DMA) Solution and incubated 1 min at room temperature before being added to the substrate-iodide mixture.

COMPARATIVE EXAMPLE Ia (CAT Only) (Glycine-Tyrosine)

Same procedures as Example I, except: The reaction mixture consisting of substrate-iodide-CAT was incubated 0.5, 3 or 6 minutes before adding the Sodium Thiosulfate Solution.

INVENTION EXAMPLE IIa (CAT+DMA Solution with Various Incubation Times) (Glycine-Tyrosine only)

Same procedures as Example II, except: The reaction mixture consisting of substrate-iodide-CAT-DMA was incubated 0.5, 3 or 6 minutes before adding the Sodium Thiosulfate Solution.

INVENTION EXAMPLE IIb & IIc ICAT+DMA Solution with Various Incubation Times and DMA/CAT Ratios) (Glycine-Tyrosine only)

Same procedures as Example II, except:
IIb—The DMA+CAT Mixture was incubated for 1, 2, or 3 minutes before addition to the substrate-iodide mixture (reaction time=30 sec.).
IIc—The ratio of DMA/CAT was either 1 or 5 (incubation time=1 min.; reaction time=30 sec.).

INVENTION EXAMPLE IId & IIe (CAT+dialkyl amine Solution)

Same procedures as Example II, except:
IId—Dibutylamine+CAT Mixture was incubated for 1, 2, or 3 minutes before addition to the substrate-iodide mixture (reaction time=30 sec.).
IIe—Diisopropylamine+CAT Mixture was incubated for 1, 2, or 3 minutes before addition to the substrate-iodide mixture (reaction time=30 sec.).

COMPARATIVE EXAMPLE III (Iodobeads ® Example) (Glycine-Tyrosine only)

5 μl Substrate (Gly-Tyr) Solution
+5 μl NaI Carrier Solution
+35μ 0.5M, pH,75 Phosphate Buffer
+5 μl NaI Labeled Solution
MIX
ADD two (2) Iodobeads ®
STAND 1 minute
REMOVE 30 μl aliquot
RUN TLC (see Example I)

INVENTION EXAMPLE IV (Iodobeads ®+DMA Example) (Glycine-Tyrosine only)

Same procedures as Example III, except:
5 μl DMA Solution
+30 μl 0.5M, pH 7.5 Phosphate Buffer was substituted for 30 μl of buffer solution.

INVENTION EXAMPLE IVa (Iodobeads ®+DMA with Incubation Example) (Glycine-Tyrosine only)

Same procedures as Example IV, except:
Two (2) Iodobeads ®
+5 μl DMA Solution
+30 μl 0.5M, pH 7.5 Phosphate Buffer were incubated for 1 minute at room temperature before being added to the substrate-iodide mixture.

EXAMPLE SOLUTIONS

Substrate Solution (Gly-Tyr)—1 mg/ml Glycine-Tyrosine in 0.5M., pH 7.5 Phosphate Buffer.
Substrate Solution (NAD)—1 mg/ml NAD analog in 0.5M., pH 7.5 Phosphate Buffer.
NaI Carrier Solution—1.5 mg/ml NaI in 0.5M., pH 7.5 Phosphate Buffer.
NaI Labeled Solution—13,000 cpm/μl of NaI$^{125}$ in 0.005M., pH 7.5 Phosphate Buffer.
CAT Solution—5 mg/ml Chloramine-T in 0.05M., pH 7.5 Phosphate Buffer.
Sodium Thiosulfate Solution—5 mg/ml Na$_2$S$_2$O$_4$ in 0.05M. pH 7.5 Phosphate Buffer.
DMA Solution—2 mg/ml dimethylamine in 0.5M. pH 7.5 Phosphate Buffer.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation. It will be obvious that certain changes and modifications may be practiced within the scope of the appended claims.

We claim:

1. A method of non-destructively radiolabelling a biomolecule substrate by halogenation, comprising the steps of:
   (a) reacting a secondary amine with a chlorinating agent to produce an N-chloro secondary amine,
   (b) reacting said N-chloro secondary amine with a radiolabelled halide salt to produce a radiolabelled elemental halogen,
   (c) reacting a solution of a biomolecule substrate with said radiolabelled elemental halogen, wherein said radiolabelled elemental halogen reacts directly with said biomolecule substrate to produce a radiohalogenated biomolecule, and
   (d) recovering a radiohalogenated biomolecule from the reaction of step (c).

2. The method of claim 1, wherein said radiohalogenated biomolecule is recovered by preparative high pressure liquid chromatography.

3. The method of claim 1, wherein said secondary amine is selected from dialkylamines.

4. The method of claim 1, wherein said secondary amine is selected from the group consisting of dimethyl amine, diethylamine, diisopropylamine, dibutylamine, morpholine and piperidine (PIP).

5. The method of claim 1, wherein the cation of said radiolabelled halide salt is selected from the group consisting of sodium, potassium, lithium, rubidium, cesium, magnesium, calcium and ammonium.

6. The method of claim 1, wherein said chlorinating agent is selected from the group consisting of chloramine-T, chloramine-T bonded to polymer beads, halazone, N-chlorosuccinimide, tetrachloroglycoluril, sodium hypochlorite, hypochlorus acid and elemental chlorine.

7. The method of claim 1, wherein the biomolecule substrate is selected from the group consisting of amino acids, peptides, proteins, drug molecules, drug metabolites, antibodies, probes and diagnostic reagents.

8. A method of producing a radiolabelled halogenating agent for non-destructively radiolabelling a substrate by halogenation, comprising the steps of:
   (a) reacting a secondary amine with a chlorinating agent to produce an N-chloro secondary amine, and
   (b) reacting said N-chloro secondary amine with the salt of a radiolabelled halogen to produce a radiolabelled halogenating agent.

9. A method of non-destructively radiolabelling a biomolecule substrate by radioiodination, comprising the steps of:
   (a) mixing dry chloramine-T powder or chloramine-T bonded to polymer beads, with a solution of a secondary amine to reduce the oxidation potential of chloramine-T, to form a mixture,
   (b) shaking said mixture until all the chloramine-T powder of chloramine-T bonded to polymer beads has dissolved,
   (c) adding a solution of KI* or NaI* to said mixture of step (b), wherein I* represents a radioisotope of iodine,
   (d) shaking said mixture of step (c) for a time sufficient to release $I_2^*$ in solution,
   (e) adding a solution of a biomolecule substrate to said mixture of step (d),
   (f) shaking the resulting mixture of step (e) until the brown color disappears, and
   (g) recovering the radioiodinated biomolecule.

10. The method of claim 9, wherein said secondary amine is piperidine (PIP) buffered at about pH 6.0 in molar excess over chloramine-T powder.

11. The method of claim 9, wherein dry chloramine-T powder is mixed with the said secondary amine in step (a).

12. The method of claim 9, wherein chloramine-T bonded to polymer beads is mixed with said secondary amine in step (a).

13. The method of claim 9, wherein said secondary amine is selected from dialkyl amines.

14. The method of claim 9, wherein said secondary amine is selected from the group consisting of diisopropylamine, dibutylamine and piperidine (PIP).

15. The method of claim 9, wherein said time sufficient to release $I_2^*$ in solution is about 30 seconds.

16. A kit for non-destructively radiolabelling biomolecules by halogenation, comprising
   (a) a vial comprising a chlorinating agent,
   (b) a vial comprising a solution of a secondary amine,
   (c) a vial comprising a solution of a salt of a radiolabelled halogen, and
   (d) instructions for use.

17. The kit of claim 16, wherein said secondary amine is selected from dialkylamines.

18. The kit of claim 16, wherein said secondary amine is selected from the group consisting of diisopropylamine, dibutylamine and piperidine (PIP).

19. A method of non-destructively radiolabelling a biomolecule substrate by halogenation, comprising the steps of:
   (a) mixing dry chloramine-T powder or chloramine-T bonded to polymer beads, with a solution of a secondary amine in molar excess over said chloramine-T powder or chloramine-T bonded to polymer beads, to form a mixture,
   (b) shaking said mixture until all the chloramine-T powder or chloramine-T bonded to polymer beads has dissolved,
   (c) adding a solution of KX* or NaX* to said mixture of step (b), wherein X* is a radioisotope of a halogen,
   (d) shaking said mixture of step (c) for a time sufficient to release X* in solution,
   (e) adding a solution of a biomolecule substrate to said mixture of step (d),
   (f) shaking the resulting mixture of step (e) until the color disappears, and
   (g) recovering the radiohalogenated biomolecule.

20. The method of claim 19, wherein X* is selected from the group consisting of radioactive iodide or bromide.

21. The method of claim 20, wherein said radioactive iodide is selected from the group consisting of $^{121}I$, $^{135}I$ and said radioactive bromide is $^{77}Br$.

22. The method of claim 20, wherein X* is radioactive iodide.

* * * * *